United States Patent
Smith et al.

(10) Patent No.: US 11,324,462 B2
(45) Date of Patent: May 10, 2022

(54) METHODS AND SYSTEMS FOR FAST FILTER CHANGE

(71) Applicant: General Electric Company, Schenectady, NY (US)

(72) Inventors: Brandon Allan Smith, Waukesha, WI (US); Holly McDaniel, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 773 days.

(21) Appl. No.: 15/813,068

(22) Filed: Nov. 14, 2017

(65) Prior Publication Data

US 2019/0142354 A1    May 16, 2019

(51) Int. Cl.
| | | |
|---|---|---|
| *A61B 6/00* | (2006.01) | |
| *A61B 6/03* | (2006.01) | |
| *A61B 6/04* | (2006.01) | |
| *G21K 1/10* | (2006.01) | |

(52) U.S. Cl.
CPC ............ *A61B 6/4035* (2013.01); *A61B 6/032* (2013.01); *A61B 6/0407* (2013.01); *A61B 6/481* (2013.01); *A61B 6/482* (2013.01); *A61B 6/5205* (2013.01); *A61B 6/54* (2013.01); *A61B 6/542* (2013.01); *G21K 1/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,108,403 | A * | 8/2000 | Cooper, III | G21K 1/10 378/156 |
| 6,173,039 | B1 * | 1/2001 | Hampel | A61B 6/032 378/147 |
| 8,325,879 | B2 | 12/2012 | Loos et al. | |
| 8,483,363 | B2 | 7/2013 | Bertram et al. | |
| 2008/0279337 | A1 * | 11/2008 | Yuan | A61B 6/4035 378/156 |
| 2015/0117593 | A1 * | 4/2015 | Ji | A61B 6/5205 378/5 |
| 2016/0078619 | A1 * | 3/2016 | Hsieh | A61B 6/06 378/4 |
| 2016/0209336 | A1 * | 7/2016 | Sung | G01N 23/04 |
| 2017/0000440 | A1 * | 1/2017 | Okerlund | A61M 5/007 |

* cited by examiner

*Primary Examiner* — Yi-Shan Yang (57) ABSTRACT

Methods and systems are provided for fasting switching a filter of an imaging system during scan. In one embodiment, a method comprises determining a first contrast enhancement of an injected contrast agent; responsive to the first contrast enhancement being higher than a first threshold, acquiring a first dataset by transmitting a radiation beam to an imaging subject via a first filter; switching to a different, second filter; acquiring a second dataset by transmitting the radiation beam to the imaging subject via the second filter, wherein an average contrast enhancement of the injected contrast agent during the acquisition of the first dataset is substantially the same as an average contrast enhancement of the injected contrast agent in the imaging subject during the acquisition of the second dataset.

8 Claims, 8 Drawing Sheets

FIG. 9B

METHODS AND SYSTEMS FOR FAST FILTER CHANGE

FIELD

Embodiments of the subject matter disclosed herein relate to diagnostic medical imaging, and more particularly, to contrast enhanced computed tomography imaging.

BACKGROUND

Noninvasive imaging modalities may transmit energy in the form of radiation into an imaging subject. Based on the transmitted energy, images may be subsequently generated indicative of the structural or functional information internal to the imaging subject. In computed tomography (CT) imaging, radiation transmits from a radiation source to a detector through the imaging subject. A bowtie filter may be positioned between the radiation source and the imaging subject for adjusting the spatial distribution of the radiation energy based on the anatomy of the imaging subject. For example, a human body in the axial plane is thicker in the middle and thinner on the periphery. The bowtie filter may be designed to distribute higher radiation energy to the middle and less radiation energy to the peripheral of the subject. As a result, the amplitude of signal received by the imaging detector is equalized, and the radiation dose on the periphery of the imaging subject is reduced. Different anatomy of the subject may require different bowtie filters. For example, bowtie filters of different shape and size may be designed to image the head, the chest, and the abdomen of the human body.

To further enhance contrast of specific organ and/or tissue type, an external contrast agent may be injected into the imaging subject. The duration for acquiring the contrast enhanced images may be short due to limited contrast agent circulation time at the anatomy being imaged. Therefore, a method for acquiring high quality contrast enhanced images across different anatomies of the subject, wherein different bowtie filters are required for imaging each of the anatomies, is needed.

BRIEF DESCRIPTION

In one embodiment, a method comprises determining a first contrast enhancement of an injected contrast agent within an imaging subject; responsive to the first contrast enhancement being higher than a first threshold, acquiring a first dataset of the imaging subject by transmitting a radiation beam to the imaging subject via a first filter; switching to a different, second filter after acquiring the first dataset; and acquiring a second dataset of the imaging subject by transmitting the radiation beam to the imaging subject via the second filter, wherein an average contrast enhancement of the injected contrast agent in the imaging subject during the acquisition of the first dataset is substantially the same as an average contrast enhancement of the injected contrast agent in the imaging subject during the acquisition of the second dataset.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
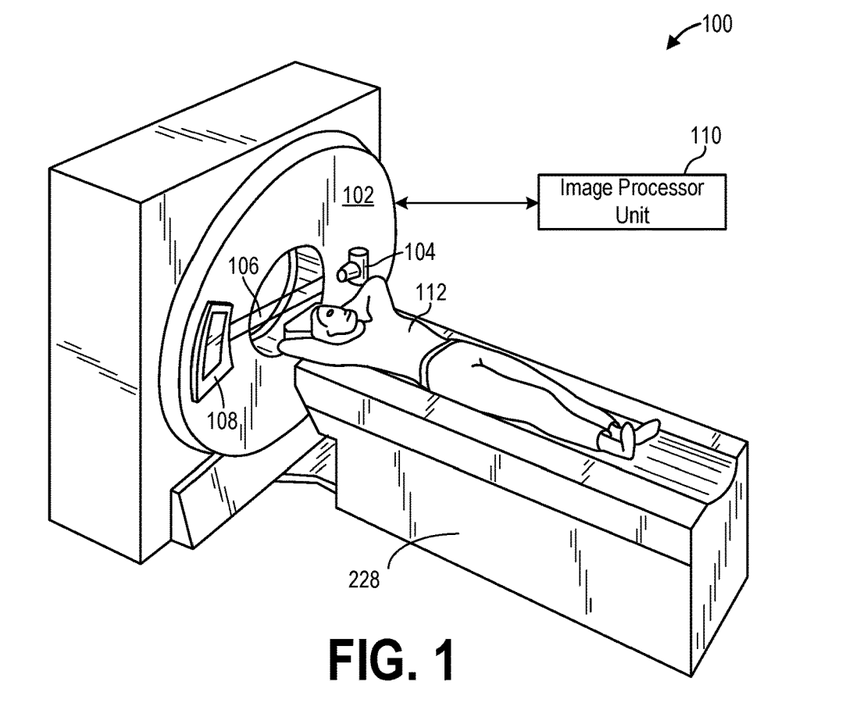
FIG. 1 shows a pictorial view of an imaging system according to an embodiment of the invention.
Figure 2:
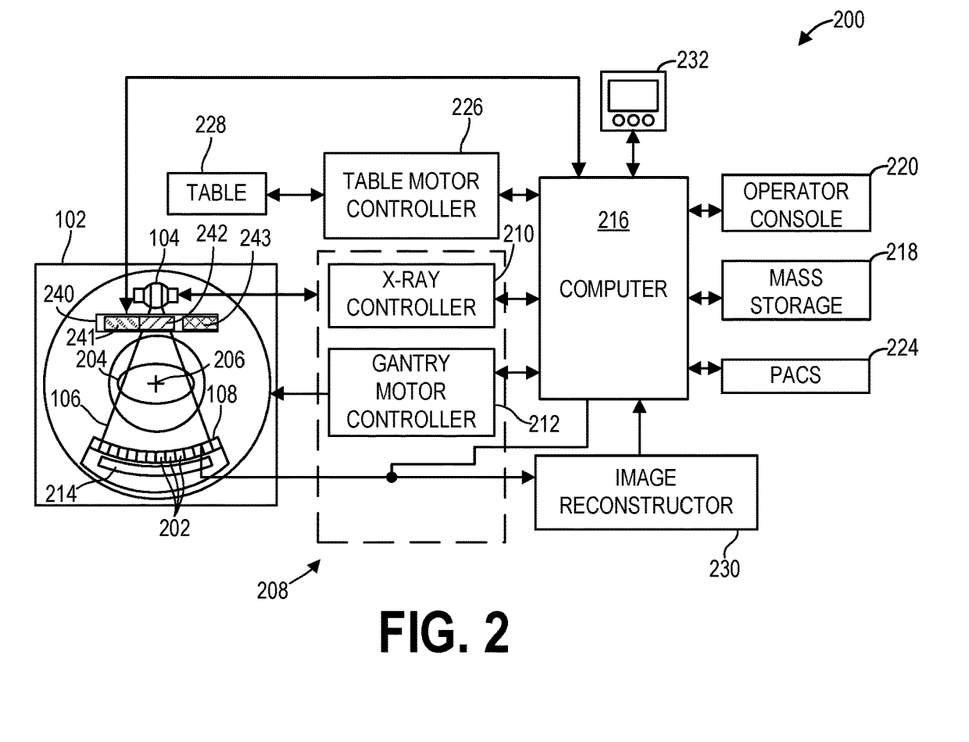
FIG. 2 shows a block schematic diagram of an exemplary imaging system according to an embodiment of the invention.
Figure 3:
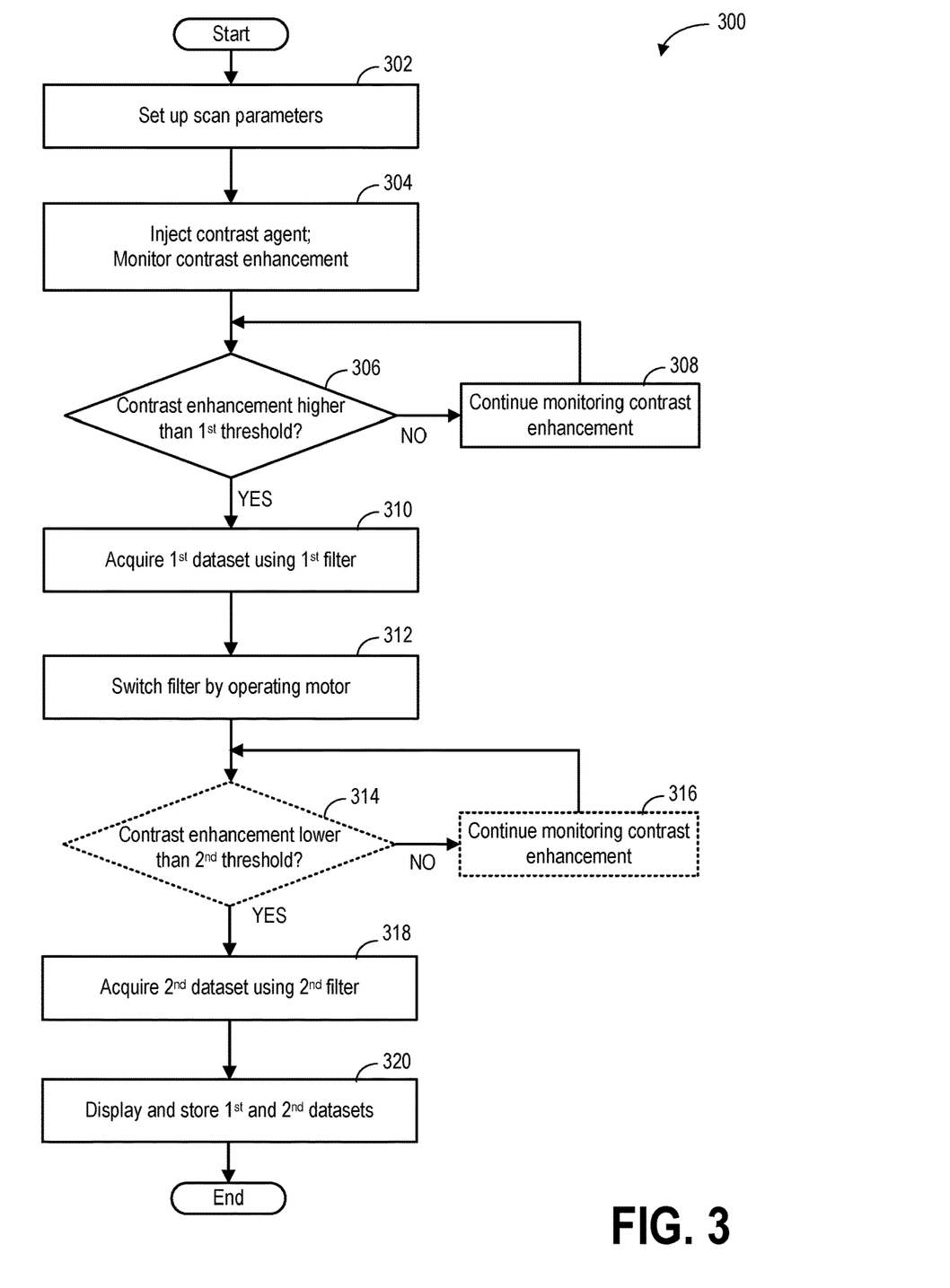
FIG. 3 shows flow chart of an example method for contrast enhanced imaging using multiple filters.
Figure 4A:
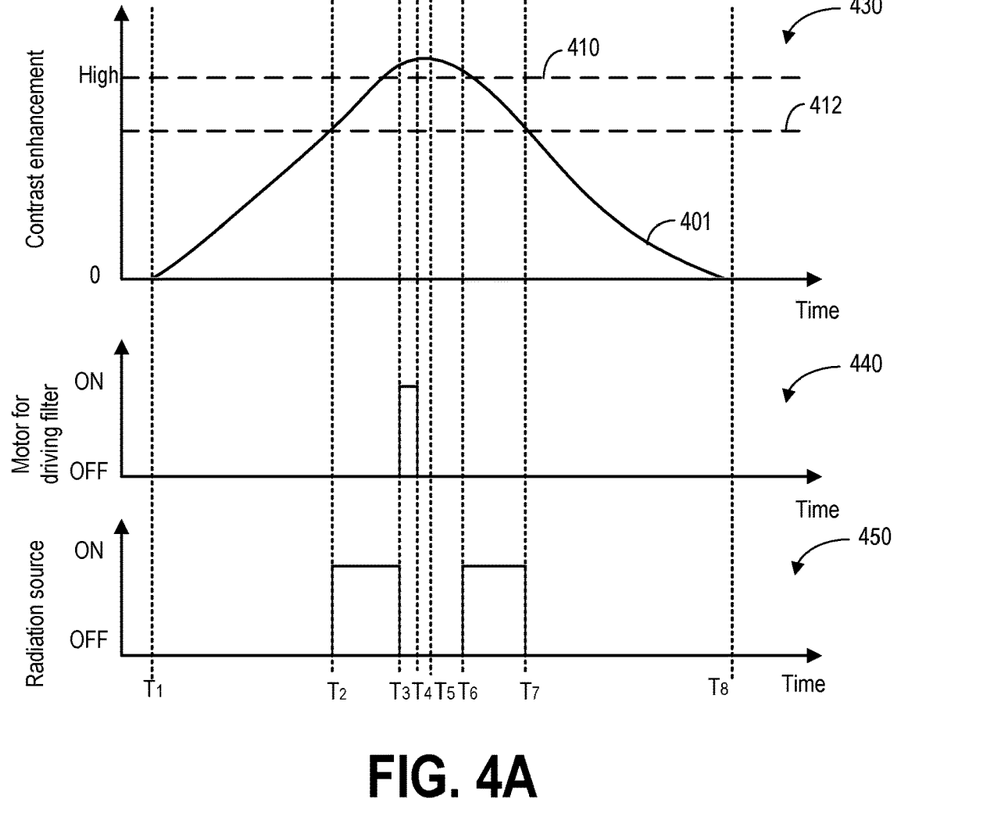
FIG. 4A shows an example timeline of contrast enhanced imaging according to the example method of FIG. 3.
Figure 4B:
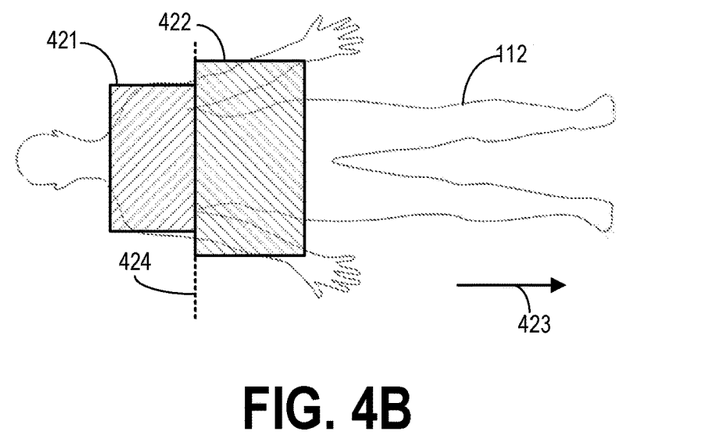
FIG. 4B illustrates sections of an imaging subject that is imaged during the example timeline of FIG. 4A.
Figure 5:
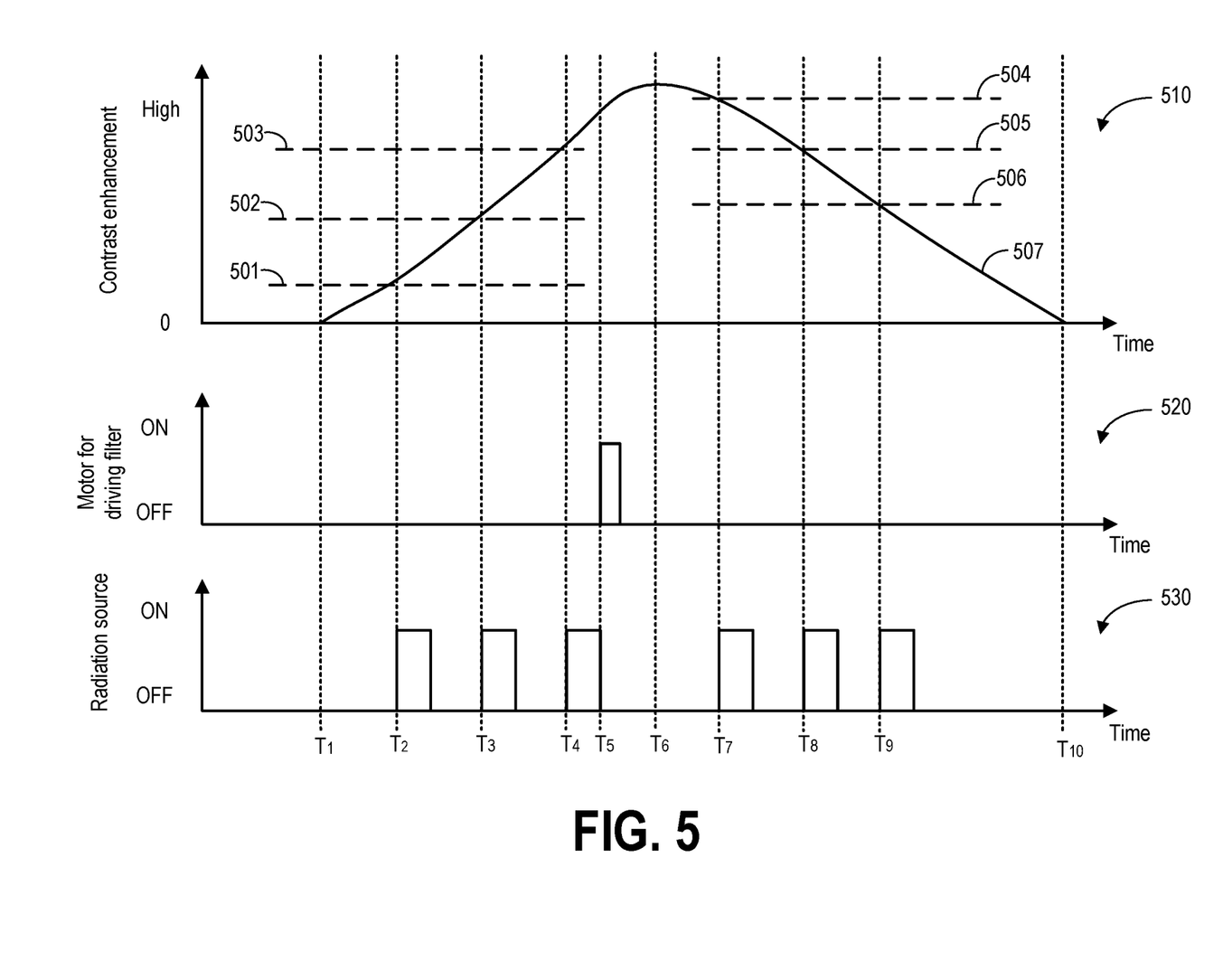
FIG. 5 shows another example timeline of contrast enhanced imaging according to the example method of FIG. 3.
Figure 6:
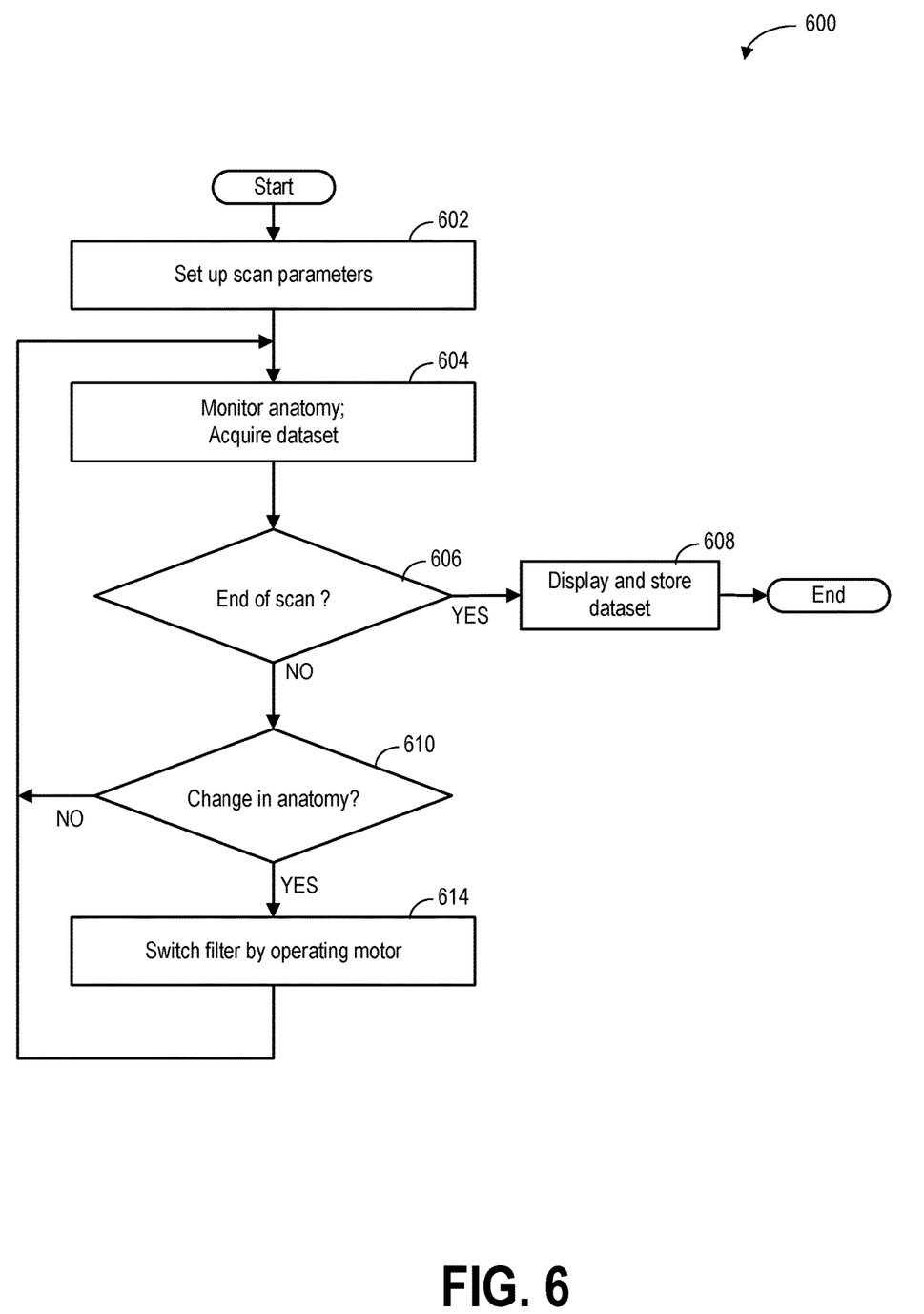
FIG. 6 shows flow chart of an example method for imaging multiple sections of an imaging subject with different anatomies.
Figure 7:
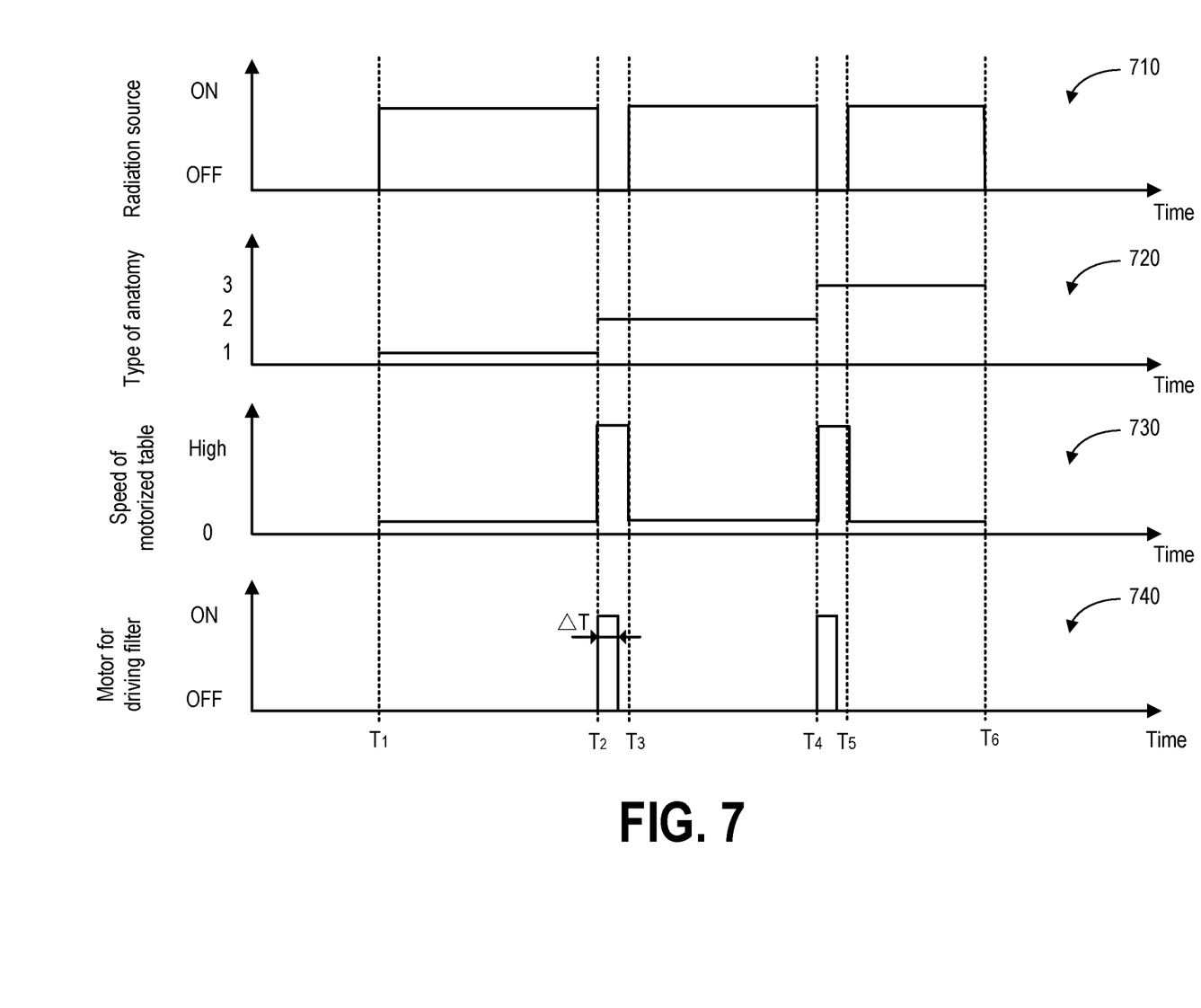
FIG. 7 shows an example timeline while implementing the method of FIG. 6.
Figure 8A:
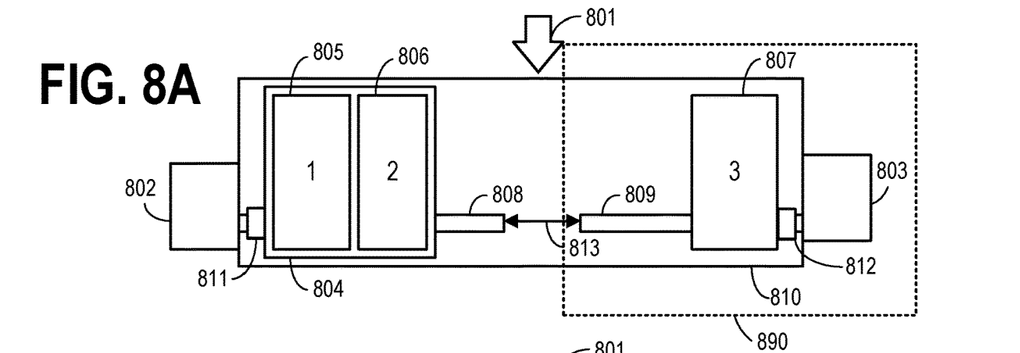
FIG. 8A shows a first position of a filter assembly with three filters.
Figure 8B:
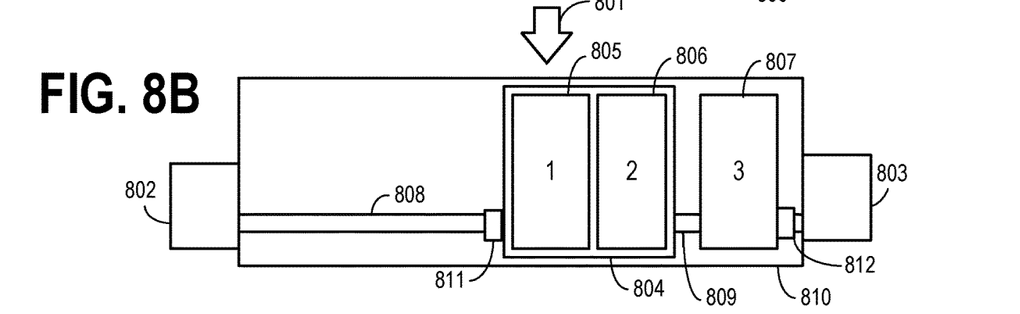
FIG. 8B shows a second position of the filter assembly of FIG. 8A.

The following description relates to various embodiments of contrast enhanced imaging. In particular, systems and methods are provided for contrast enhanced CT imaging using more than one bowtie filter. FIGS. 1-2 show an example embodiment of an imaging system, wherein a filter is positioned between the radiation source and the imaging subject. Different filters may be selected based on the anatomy of the imaging subject being imaged. FIG. 3 shows an example method of contrast enhanced CT imaging with fast switching bowtie filters. In particular, after contrast agent injection, the bowtie filter is switched before imaging a different section of the subject by operating a filter driving system. FIG. 4A shows an example timeline of CT imaging and filter switching with respect to the contrast agent enhancement in the imaging subject. FIG. 4B illustrates sections of the subject that have been imaged during the timeline of FIG. 4A. FIG. 5 shows another example timeline of CT imaging and filter switching, wherein images are acquired at multiple time points to track variation of the contrast enhancement in the subject over time. The fast filter switching may also be used for fast imaging of multiple sections of the imaging subject, as shown in FIGS. 6-7. FIGS. 8A-8D show various positions of an example filter assembly with three filters. FIGS. 9A-9B show detailed configuration of the filter driving system.

Though a CT system is described by way of example, it should be understood that the present techniques may also be useful when applied to images acquired using other imaging modalities, such as tomosynthesis, C-arm angiography, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which a radiation source projects a fan- or cone-shaped beam that is collimated to lie within an x-y plane of a Cartesian coordinate system and generally referred to as an "imaging plane." The x-ray beam passes through an imaging subject, such as a patient. The beam, after being attenuated by the imaging subject, impinges upon an array of radiation detectors. The intensity of the attenuated radiation beam received at the detector array is dependent upon the attenuation of an x-ray beam by the imaging subject. Each detector element of the array produces a separate electrical signal that is a measurement of the beam intensity at the detector location. The intensity measurement from all the detectors is acquired separately to produce a transmission profile.

In third-generation CT systems, the radiation source and the detector array are rotated with a gantry within the imaging plane and around the object to be imaged such that the angle at which the x-ray beam intersects the imaging subject constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the imaging subject. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a display.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

FIG. 2 illustrates an exemplary imaging system 200 similar to the CT system 100 of FIG. 1. In accordance with aspects of the present disclosure, the system 200 is configured to perform automatic exposure control responsive to user input. In one embodiment, the system 200 includes the detector array 108 (see FIG. 1). The detector array 108 further includes a plurality of detector elements 202 that together sense the x-ray beam 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

A bowtie filter housing 240 may be mounted within gantry 102 between radiator source 104 and the subject 204. The bowtie filter may change the energy distribution of the radiation beam in the axial plane of the imaging subject (such as a patient). For example, the re-distributed radiation beam may have higher energy at the center and lower energy at the periphery of the subject. One or more bowtie filters may be positioned within the filter housing 240. Each and every bowtie filter is rigid and non-deformable. Each of the bowtie filters may be designed to image a specific anatomy or section of the human body, such as head, chest, and abdomen. Three different bowtie filters 241, 242, and 243 are shown in FIG. 2 as an example. The bowtie filters are shown here in rectangular shape as an example. The bowtie filters alternatively be in different shapes and materials to provide proper x-ray special spectrum for imaging various types of anatomies. During imaging, one of the bowtie filters may be selected based on the anatomy of the subject, and be placed into the radiation beam path. Responsive to a change in the anatomy, the filter may be changed from one to another. Example arrangement of the filters in the filter housing is shown in FIGS. 8A-8D. A filter driving system (not shown here) may be coupled to the filter to move the filter into and out of the radiation beam path. Examples of the filter driving system are shown in FIGS. 9A-9B. In one embodiment, the motor may couple the filters through a shaft. The bowtie filters may be switched from one to another by translating the filters along the shaft by rotating the shaft with a motor. One of the filters may be selected and translated into the x-ray beam between the radiation source and the imaging subject to image a specific section of the human body. Computing device 216 may send command to the motor of the filter driving system to move the selected filter in to the radiation beam. The filter driving system may also send filter position information back to the computing device 216.

In certain embodiments, the system 200 is configured to traverse different angular positions around the subject 204 for acquiring desired projection data. Accordingly, the gantry 102 and the components mounted thereon (such as the radiation source 104, the filter housing 240, and the detector 202) may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

Turning to FIG. 3, an example method 300 for performing contrast enhanced imaging with multiple filters is presented. To achieve high image quality, it is optimal to perform the contrast enhanced imaging at high radiation attenuation of the targeting anatomy. In other words, it is optimal to perform the contrast enhanced imaging at high contrast agent enhancement. The amount of the attenuation, or the degree of contrast enhancement, may be measured by the CT numbers. For example, increased attenuation or increased contrast enhancement corresponds to high CT numbers. Further, it is preferable to minimize the dose of the contrast agent and the number of contrast injections during scan. Method 300 achieves fast image acquisition of multiple anatomies of the imaging subject by fast changing the filters during the scan.

Method 300 may be performed according to instructions stored in the non-transitory memory in a computing device (such as computer 216 of FIG. 2) of the imaging system. In particular, after the contrast agent is injected into the imaging subject, a first section of the subject is imaged using a first filter. After fast filter switching, a second, different, section of the subject is imaged with a second filter. The first and the second sections may have different anatomies. As such, contrast enhanced images of different anatomies of the subject may be acquired with a one-time contrast agent injection. Herein, a section of the subject is a three-dimensional volume along the length of a human body.

At 302, method 300 includes setting up scan parameters. For example, a user may input or select the scan parameters according to a scanning protocol or a menu. The scan parameters may include the type and sequence of the filters that are going to be used during the scan. The type of the filters may be chosen based on the anatomy of imaging subject that is to be imaged. Method 300 may also include setting scan timing. As one example, the scan timing may include a start time and a duration for imaging each section. As another example, method 300 may include setting up one or more contrast enhancement thresholds, and the imaging of each section may start responsive to the actual contrast agent enhancement reaching the thresholds. Method 300 may also include loading anatomy information of the imaging subject to the memory of the computation device. The anatomy information may be acquired from a pre-scan. This step may also include moving the first filter to a position in the x-ray beam path between the radiation source and the subject, and moving the subject so that the first section of the subject is within the gantry for imaging. The type of the first filter is determined based on the anatomy of the first section of the subject.

At 304, contrast agent is injected into the imaging subject. Method 300 starts monitoring the enhancement of the contrast agent within the subject, at the anatomy of interest. As one example, the contrast agent enhancement at the anatomy of interest may be monitored by periodically imaging the same location of the subject and analyzing the change if contrast enhancement over time. As another example, the enhancement of the contrast agent in one section of the subject may be derived from the contrast enhancement in another section of the subject. As yet another example, the contrast enhancement may be estimated based on time elapsed since injection based on empirical knowledge of the physiological circulation time of the contrast agent in the anatomy of interest. As one example, the physiological circulation time of the contrast agent may be the circulation time of blood. The estimated enhancement may further be adjusted based on the dose of the contrast and the mass of the subject. For example, the estimated enhancement may increase with the increased contrast dose and decrease with the mass of the subject.

At 306, method 300 compares the estimated contrast agent enhancement with a predetermined positive non-zero first threshold. The first threshold may be determined based on a predicted minimum concentration of the contrast agent in the subject, as well as the duration and sequence of image acquisition as defined by the scan parameters described above. The first threshold may be a sensitivity of the imaging system to the contrast agent in the imaged anatomy. In one example, the first threshold may be determined so that each dataset of each section of the subject is acquired at an enhancement (CT number) higher than the threshold. For example, the first threshold may be slightly lower than a predicted maximum enhancement, such as 10% lower than the predicted maximum enhancement. In this way, a plurality of imaging datasets may be obtained when the contrast enhancement is within a threshold range of the maximum enhancement (e.g., as the enhancement approaches, reaches, and then recedes from the maximum enhancement threshold). In one embodiment, the contrast agent enhancement in a first section of the subject is compared with the first threshold.

Responsive to the estimated enhancement being higher than the first threshold, method 300 proceeds to 310 to acquire an image dataset. Otherwise, method 300 moves to 308 to continue monitoring contrast agent enhancement.

At 310, method 300 starts acquiring the first dataset of the first section of the subject using the first filter. For example, the radiation source (such as 104 of FIGS. 1-2) may be activated, and start emitting radiation exposure (such as 106 of FIGS. 1-2) to the imaging subject through the first filter. The dataset is acquired from the detector (such as 108 of FIG. 2) upon receiving the attenuated radiation beam from the imaging subject. Herein, a dataset corresponds to the projection data acquired during imaging a section of the subject. In one example, the first section of the subject may be imaged once. In another example, the first section of the subject may be imaged multiple times to capture the change of enhancement of the contrast agent in the subject.

At 312, after acquiring the first dataset, the first filter is moved out of the radiation beam path and the second filter is moved into the radiation beam path. The first and the second filters may be moved by operating one or more motors, such as shown in FIGS. 8A-8B, which show example filter driving systems. By moving the filters with a motor, filters may be automatically switched quickly within one scan. In one example, switching one filter with another filter may be completed within two seconds. Step 312 may also include moving the subject via the motorized table (such as motorized table of 228 in FIGS. 1-2) to a proper location to start acquiring a second dataset. The filter switching and subject relocation may be performed simultaneously. The type of the second filter may be determined based on the anatomy of a second section of the subject. The first section and the second section of the subject may have different anatomies (such as different size and shape), so that different filter types are used for imaging each section. As an example, the first section may be the chest and the second section may be the abdomen. As another example, the first section may be one of the chest, the head, and the abdomen, and the second section may be one of the head, the chest, and the abdomen.

At 314, method 300 estimates the enhancement of the contrast agent and compares it with a predetermined second threshold. Similar to 304, the contrast agent enhancement may be monitored by periodically imaging at the same location of the subject and analyzing the contrast enhancement over time. The contrast agent enhancement may alternatively be determined based on time elapsed since injection, the physiological circulation time of the anatomy of interest, the dose of the contrast, and the mass of the subject. The second threshold may be determined so that the average contrast enhancement while acquiring the first dataset is substantially the same as the average contrast enhancement while acquiring the second dataset. Herein, the average contrast enhancements are substantially the same means the difference between the average contrast enhancements is within a threshold range. For example, the difference between the average contrast enhancements is within 1% (or other suitable range, such as 5%) of either the average contrast enhancement of the first dataset or the second dataset. In another embodiment, the second threshold may be determined so that the average contrast enhancement while acquiring the first dataset is the same as the average contrast enhancement while acquiring the second dataset. As such, the degree of contrast enhancement of the first and the second datasets are the same. In one example, the second threshold may be higher than the first threshold. In one embodiment, the contrast agent enhancement in the second section of the subject is compared with the second threshold.

If the contrast enhancement is lower than the second threshold, method 300 proceeds to 316 to acquire the second dataset. Otherwise, method 300 continues to monitor contrast agent enhancement. In one embodiment, steps 314 and 316 may be skipped, and the second dataset is acquired immediately after filter switching at 312. Further, in some examples, the second dataset may be acquired when the contrast agent enhancement is lower than the second threshold yet still higher than the first threshold. In this way, the second dataset may be acquired after the contrast agent enhancement has reached the maximum enhancement and is at the approximate same enhancement as when the first dataset was collected.

At 318, the second dataset of the second section of the subject is acquired with the second filter. At least in some examples, due to the fast switching of the filters, no additional contrast agent is injected to the imaging subject between the acquisition of the first dataset and the acquisition of the second dataset. As one example, the second section of the subject may be imaged once. As another example, the second section of the subject may be imaged multiple times to capture the change of enhancement of the contrast agent in the subject.

At 320, the acquired first and second datasets are displayed and stored. In one embodiment, the first dataset and the second dataset may be re-constructed to form an image. The image may include the first and the second sections displayed on the display. The image may be two-dimensional or three-dimensional. As one example, the re-constructed first and second datasets may be displayed with the same dynamic range (that is, the same range of signal amplitudes in the datasets are displayed), as the average contrast enhancement is substantially the same for the first and the second dataset. As such, images of the first and the second sections of the subject are comparable to each other, and diagnosis may be made by analyzing the images acquired with one contrast agent injection. In another embodiment, data of the first and the second datasets that have the same average contrast enhancement may be selected, and then processed to be displayed together in one image. Images of the first and second sections of the subject acquired at various contrast enhancement may be generated to provide functional information of the imaged organs. The first and the second dataset, as well as the processed images may be saved in the storage of the imaging system.

Turning to FIG. 4A, an example timeline of contrast enhancement 430, status of the motor for driving the filters 440, and the status of the radiation source 450 while implementing method 300 are shown. In graph 430, the y-axis is the enhancement of contrast agent in the imaging subject. The contrast enhancement increases as indicated by the arrow of the y-axis. Curve 401 shows the contrast enhancement over time. In one example, curve 401 may be predetermined based on empirical knowledge (such as physiological circulation time) of the contrast agent, the dose, and the mass of the subject. In another example, curve 401 may be estimated or measured during the contrast enhanced imaging. For example, the contrast enhancement may be periodically estimated or measured. Curve 401 may be then generated by interpolating the estimated/measured contrast enhancement. In graph 440, the motor status may be on or off. When the motor is on, filters are switched. For example, the motor may be activated to rotate a shaft coupled to the filters. By rotating the shaft, the filter may be translated into and out of the radiation beam path. In graph 450, the radiation source status may be on or off. When the radiation source is on, dataset of the imaging subject is acquired. In FIG. 4A, the x-axes indicate time. The time increases as indicated by the arrows of the x-axes.

Prior to T1, scan parameters are set up. The first filter is positioned into the radiation beam path. At T1, contrast agent is injected into the subject. Responsive to the contrast agent administration, the contrast enhancement increases with time from zero.

At T2, the contrast enhancement reaches the first nonzero threshold 412. Responsive to the contrast enhancement higher than the first threshold 412, the radiation source is turned on, and acquisition of the first dataset of the first section of the subject is started. Acquisition of the first dataset proceeds from T2 to T3. FIG. 4B shows an example first section 421 of the subject 112. The first section covers the chest, and the first filter is designed to image the chest. To complete the scan of the first section, a sequence of axial scans may be performed in the direction along the length of the subject, as shown with arrow 423.

At T3, the imaging of the first section of the imaging subject ends, and the radiation source is turned off. Right after the acquisition of data during the first scan at T3, the filters are switched by activation of the motor, and the first filter is moved out of the path of radiation and the second filter is moved into the path. At T4, the filter switching is completed. Due to the fast switch of the filter, the average contrast enhancement is high during imaging. The duration from T3 to T4 may be less than two seconds. In one example, the subject may be moved starting from T3 to a new location for imaging the second section of the subject. The contrast agent enhancement keeps increasing from T2 to T3 and peaks at T5. In another example, the peak T5 of the contrast enhancement may be anywhere between T3 and T6.

At T6, responsive to the contrast enhancement being lower than the second threshold 410, the second dataset is acquired from T6 to T7 with the second filter. As one example, the second threshold may be determined so that the average contrast enhancement from T2 to T3 is substantially the same as the average contrast enhancement from T6 to T7. As another example, the second threshold 410 may be higher than the first threshold 412. FIG. 4B shows an example of the second section 422 of the subject 112. The second section covers the abdomen. To complete the scan of the second section, a sequence of axial scans may be performed in the direction along the length of the subject, as shown with arrow 423. In FIG. 4B, the first section and the second section are connected to each other at location 424. That is, the acquisition of first dataset ends at 424 and the acquisition of the second dataset starts at 424. In this example, the subject is not moved after acquiring the first dataset and before acquiring the second dataset. In another embodiment, the first section and the second section may not be connected with each other, or the first section and the second section are overlapped with each other. The subject is then moved upon completion of the acquisition of the first dataset at T3. For example, the first section is the head and the second section is the abdomen, and subject is moved after acquiring the first dataset and before acquiring the second dataset. At T8, the contrast enhancement decreases to zero.

In another embodiment, contrast enhancement curve 401 may include the enhancement of contrast agent in different sections of the subject. For example, the contrast enhancement from T1 to T5 is the contrast enhancement in the first section of the subject, and the contrast enhancement from T5 to T8 is the contrast enhancement in the second section of the subject. The physiological circulation of the contrast agent may be different in different sections of the human body. For example, the physiological circulation of contrast agent in head may be longer than the physiological circulation in abdomen. By using contrast enhancement of the imaged section, optimal image quality may be achieved.

Turning to FIG. 5, another example timeline of the contrast agent enhancement 510, the status of motor for driving the filter 520, and the status of the radiation source 530 while implementing method 300 of FIG. 3 are shown. Different from FIG. 4A, herein, a plurality of datasets of the first section of the subject are acquired with the first filter at multiple time points while the contrast enhancement increases, and a plurality of datasets of the second section of the subject are acquired at multiple time points with the second filter while the contrast enhancement decreases. As such, the phases of the contrast circulation in the subject may be obtained. In graph 510, the y-axis is the enhancement of contrast agent in the imaging subject. The contrast agent enhancement increases as indicated by the arrow of the y-axis. Curve 507 shows the contrast enhancement over time. In one example, curve 507 may be predetermined based on empirical knowledge (such as physiological circulation) of the contrast agent, the dose, and the mass of the subject. In another example, curve 507 may be estimated or measured during the contrast enhanced imaging. For example, the contrast enhancement may be periodically estimated or measured. Curve 507 may be then generated by interpolating the estimated/measured contrast enhancement. In graph 520, the motor status may be on or off. When the motor is on, filters are switched. For example, the motor may be activated to rotate a shaft coupled to the filters. By rotating the shaft, the filters may be translated into and out of the radiation beam path. In graph 530, the radiation source status may be on or off. When the radiation source is on, dataset of the imaging subject is acquired. In FIG. 5, the x-axes are time. The time increases as indicated by the arrows of the x-axes.

At T1, contrast agent is injected into the subject. Responsive to the contrast agent administration, the contrast enhancement increases with time from zero. The contrast enhancement increases from T1 to T6, and decreases from T6 to zero at T10. From T1 to T6, multiple datasets of the first section of the subject are acquired using the first filter. From T6 to T10, multiple datasets of the second section of the subject are acquired using the second filter. Upon completion of imaging the first section, the first filter is moved out of the radiation path and is replaced by the second filter by actuating one or more motors in the filter driving system. The peak of the contrast enhancement curve 401 may be anywhere between T5 and T7.

Each of the datasets may be acquired responsive to the contrast enhancement reaching a predetermined nonzero threshold. For example, acquisition of the first dataset starts at T2, responsive to the contrast enhancement higher than the first threshold 501; acquisition of the second dataset starts at T3, responsive to the contrast enhancement higher than the second threshold 502; and acquisition of the third dataset starts at T4, responsive to the contrast enhancement higher than the third threshold 503. Acquisition of the fourth dataset starts at T7, responsive to the contrast enhancement lower than the fourth threshold 504; acquisition of the fifth dataset starts at T8, responsive to the contrast enhancement lower than the fifth threshold 505; and acquisition of the third dataset starts at T9, responsive to the contrast enhancement lower than the third threshold 506. The thresholds may be chosen such that the average contrast enhancement while imaging the first and the second sections are substantially the same. For example, the average contrast enhancement while acquiring the first dataset is substantially the same as the average contrast enhancement while acquiring the sixth dataset; the average contrast enhancement while acquiring the second dataset is the substantially same as the average contrast enhancement while acquiring the fifth dataset; and the average contrast enhancement while acquiring the third dataset is substantially the same as the average contrast enhancement while acquiring the fourth dataset. As such, at specific contrast enhancement, contrast enhanced images of the first and the second sections of the subject may be comparable and displayed with the same dynamic range.

Similar to FIG. 4A, in one embodiment, the contrast enhancement curve 507 may include contrast enhancement of different sections of the subject. For example, curve 507 from T1 and T6 is the contrast enhancement in the first section of the subject. Curve 507 form T6 to T10 is the contrast enhancement in the second section of the subject.

FIG. 6 shows an example method 600 for imaging multiple different anatomies of the imaging subject with fast filter switching. Method 600 may be carried out according to instructions stored in the non-transitory memory in a computing device (such as computer 216 of FIG. 2) of the imaging system.

At 602, method 600 includes setting up scan parameters. For example, a user may input or select the scan parameters according to a scanning protocol or a menu. The scan parameters may include the type and sequence of the filters that are going to be used during the scan. The type of the filters may be chosen based on the anatomy of imaging subject that is to be imaged. Method 600 may also include setting scan timing. As one example, the scan timing may include a start time and a duration for imaging each section. Method 600 may also include loading anatomy information of the imaging subject to the memory of the computation device. The anatomy information may be acquired from a pre-scan. As another example, the anatomy information may be acquired from a scout or a localized scan. This step may also include moving a filter to a position in the x-ray beam path between the radiation source and the subject, and moving the imaging subject via the motorized table (such as motorized table 228 of FIGS. 1-2) so that the proper section of the subject is within the gantry for imaging. The type of the filter is determined based on the anatomy of the currently imaged section of the subject.

At 604, method 600 starts acquiring the dataset of the imaging subject using the first filter. Simultaneously, method 600 monitors the anatomy of the imaging subject. For example, the radiation source (such as 104 of FIGS. 1-2) may be activated, and start radiation exposure (such as 106 of FIGS. 1-2) of the imaging subject through the first filter. The dataset is acquired from the detector (such as 108 of FIG. 2) upon receiving the transmitted radiation signal from the imaging subject. As one example, the anatomy of the imaging subject may be monitored by analyzing the acquired dataset. As another example, the anatomy of the imaging subject may be estimated by the currently imaged location. The currently imaged location may be calculated based on the starting location of the scan and the travel distance of the motorized table. In one embodiment, the anatomies of the subject may be grouped in different types. For example, the anatomy of a human body may be grouped based on size, into types of such as the head, the chest, and the abdomen. In one embodiment, the acquisition of the dataset may be started responsive to a contrast agent enhancement higher than a threshold.

At 606, method 600 determines whether the scan is ended. Method 600 may determines the end of the scan based on the protocol setup at 602. If the scan ends, method 600 proceeds to 608 to display and store the acquired dataset. If additional scan is needed, method 600 proceeds to 610.

At 608, the acquired dataset is displayed and stored. In one embodiment, dataset acquired from different sections of the subject may be re-constructed to form an image. The image may be two-dimensional or three-dimensional. The acquired dataset, as well as the processed images may be saved in the storage of the imaging system.

At 610, method 600 determines whether the anatomy of the imaging subject that is being imaged has changed or is about to change. In one embodiment, the anatomy may be determined to have changed when the size to type of the anatomy changes. Responsive to the change in anatomy, method 600 proceeds to 614 to switch the filter. Otherwise, method 600 moves to 640 to continue acquiring the dataset with the current filter and monitoring the anatomy.

At 614, responsive the change in anatomy, the current filter is moved out of the radiation beam path and a different filter is moved into the radiation beam path. The filters may be moved by operating one or more motors, such as motors shown in FIGS. 9A-9B. By moving the filters with a motor, filters may be automatically switched quickly within one scan. In one example, switching one filter with another filter may be completed within two seconds. Step 614 may also include moving the subject via the motorized table (such as motorized table of 228 in FIGS. 1-2) to a predetermined location. The filter switching and subject relocation may be performed simultaneously. After filter switching, method 600 continues acquiring the dataset with the new filter and monitoring the anatomy. In one embodiment, the data acquisition may be continued through the filter switching process. In this way, time delays between imaging different anatomies of the subject is reduced or avoided.

While method 600 is described above as including a filter switch that is performed in response to a detected or predicted change in imaged anatomy, other triggers for switching the filters are possible. For example, the scanning protocol selected by the operator of the imaging system may include a series of images (reconstructed from acquired projection data) to be acquired along the imaging subject. A prescribed first set of images may be acquired while a first filter is in the radiation path and while the imaging system table is at a first position. Once the first set of images has been acquired, the scanning protocol may command or instruct the table to be moved to a second position in order to move the imaging subject relative to the radiation source and detector. The scanning protocol may also command or instruct the filter driving system to move the first filter out of the radiation path and move a second filter into the radiation path. The filters may be moved/switched while the table is moving. A prescribed second set of images may then be acquired while the second filter is in the radiation path and the table is in the second position. In such a configuration, the switching of the filters may be triggered by a predetermined number of images (e.g., projection data sets) being acquired, by a predetermined amount of time having elapsed since commencement of the scanning procedure, and/or by a user input instructing the filters to be switched.

FIG. 7 shows an example timeline of the status of the radiation source 710 the type of the anatomy 720, the speed of the motorized table (such as motorized table 228 of FIGS. 1-2), and the status of the motor for driving the filters 740 while implementing method 600 of FIG. 6. In one example, the imaging system performs helical scan of different types of anatomy. In graph 710, the radiation source status may be on or off. When the radiation source is on, a dataset of the imaging subject is acquired. In graph 720, different types of the anatomy is shown. For example, the first type of the anatomy is the head, the second type of the anatomy is chest, and the third type of the anatomy is the abdomen. In graph 730, the speed of the motorized table for moving the subject is shown. The speed increases with the y-axis. In graph 740, the motor status may be on or off. When the motor is on, filters are switched. For example, the motor may be activated to rotate a shaft coupled to the filters. By rotating the shaft, the filter may be translated into and out of the radiation beam path.

At T1, the radiation source is turned on for imaging the first type of the anatomy. A filter designed for imaging the first type of anatomy is positioned between the radiation source and the imaging subject. The motorized table is moved at a nonzero speed to translate the subject through the gantry for the scan. The motor for driving the filter is off. In one embodiment, the radiation source may be started responsive to an enhancement of the contrast agent higher than a nonzero threshold.

At T2, the anatomy being imaged or to be imaged changes from the first type to the second type. Responsive to the change, the motor for driving the filter is actuated to switch the current filter to a different filter designed for imaging the second type of anatomy. The duration for switching the filter lasts $\Delta T$, which is less than two seconds. The motorized table may be operated at a different speed from prior to T2 and move the imaging subject to a section with different anatomy. As one example, the motorized table may be moved at a higher speed from T2 to T3 comparing to prior to T2. As another example, the motorized table may be stationary and the speed is zero from T2 to T3. As yet another example, the motorized table may move at the same speed as during T1-T2. While switching the filter, the radiation source is turned off and no radiation exposure is emitted to the imaging subject. As such, the overall patient radiation dose may be reduced. In one embodiment, the duration for moving the imaging subject (T2–T3) may be greater than the duration for switching the filter ($\Delta T$), and the radiation source is turned off while moving the imaging subject.

From T3 to T4, the second type anatomy is imaged and the motorized table is moved at a low speed. As one example, the speed of the motorized table from T3 to T4 is the same as the speed of the motorized table from T1 to T2.

At T4, the anatomy being imaged or to be imaged changes from the second type to the third type. Responsive to the change, the motor for driving the filter is actuated to switch the current filter to a different filter designed for imaging the third type of anatomy. During T4 to T5, the motorized table may move at a different speed from during T3-T4. The radiation source is turned off while switching the filter.

From T5 to T6, the third type anatomy is imaged and the motorized table is moved at a low speed. As one example, the speed of the motorized table from T5 to T6 is the same as the speed of the motorized table from T3 to T4.

At T6, the scan is finished. The speed of the motorized table goes to zero and the radiation source is turned off.

FIGS. 8A-8D show an example configuration of a filter assembly with three filters 805, 806, and 807 within filter housing 810. In this example, the first and second filters are positioned together in a housing 804. The housing 804 is coupled to a ballscrew 811, and can be translated along the first shaft 808 by rotating the first shaft with a first motor 802. The third filter 807 is coupled to a ballscrew 812 and can be translated along the second shaft 809 by rotating the second shaft with the second motor. A localized clearance feature (not shown) is present in the housing 804 to prevent interference of the second shaft 809 from interfering with the housing 804 as the housing 804 translates along the first shaft 808. The direction of the x-ray beam (such as x-ray radiation 106 of FIGS. 1-2) is indicated by 801. One of the three filters may be translated into the beam path of the x-ray beam by rotating one or both shafts 808 and 809 via motors 802 and 803. The first and the second shafts may be aligned in one line along the shafts, and are spaced apart from each other by a gap 813. The x-ray beam may transmit through the gap. The motor (such as motor 803), the shaft (such as shaft 809) coupled to the motor, and the filter (such as filter 807) coupled to the shaft form a filter driving system 890.

The filter assembly may include one or more filter driving systems. Example configuration of the filter driving system is shown in FIGS. 9A-9B.

FIG. 8A shows a first position of the filter assembly. The x-ray beam transmits through the filter housing without passing through any filter. The first and the second filters are at a location close to the first motor 802, and the third filter is at a location close to the second motor 803.

FIG. 8B shows a second position of the filter assembly. The x-ray beam transmits though the first filter 805 in the filter housing 810. The filter assembly may transit from the first position to the second position by actuating the first motor 802 and translating the first filter 805 into the x-ray beam path.

Figure 8C:
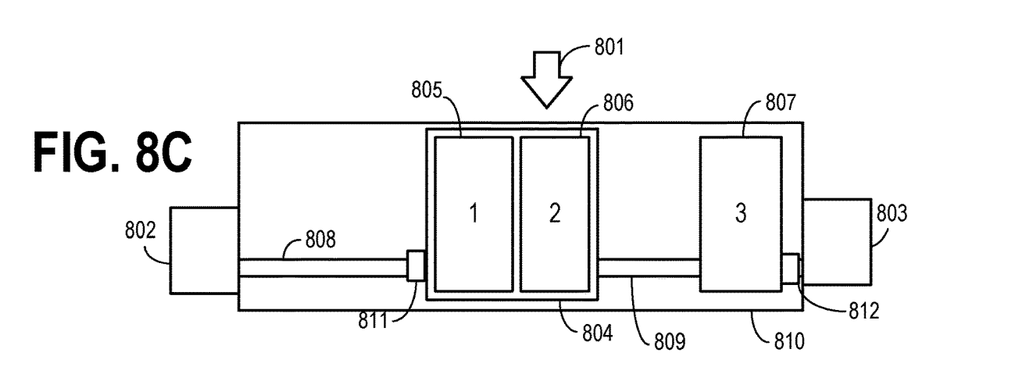
FIG. 8C shows a third position of the filter assembly of FIG. 8A.
Figure 9A:
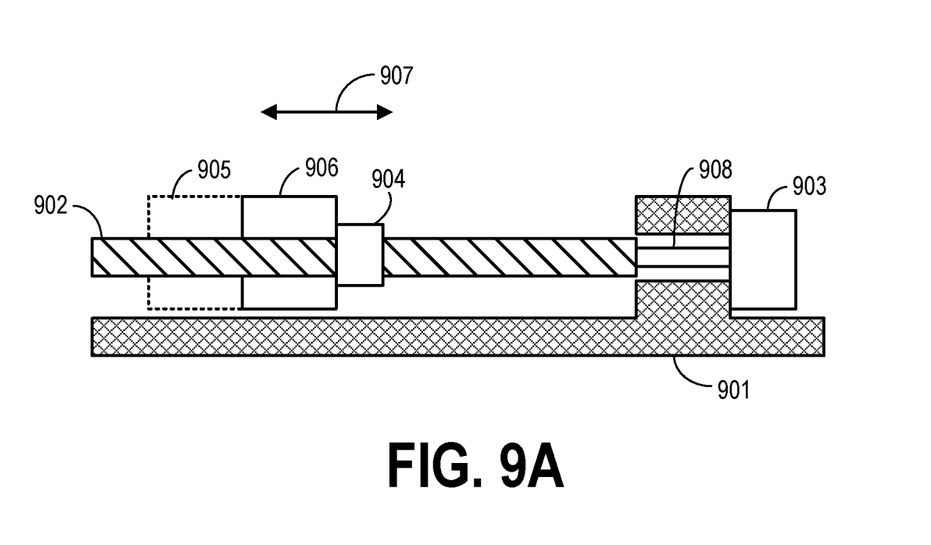
FIG. 9A shows one example configuration of a filter driving system.
Figure 9B:
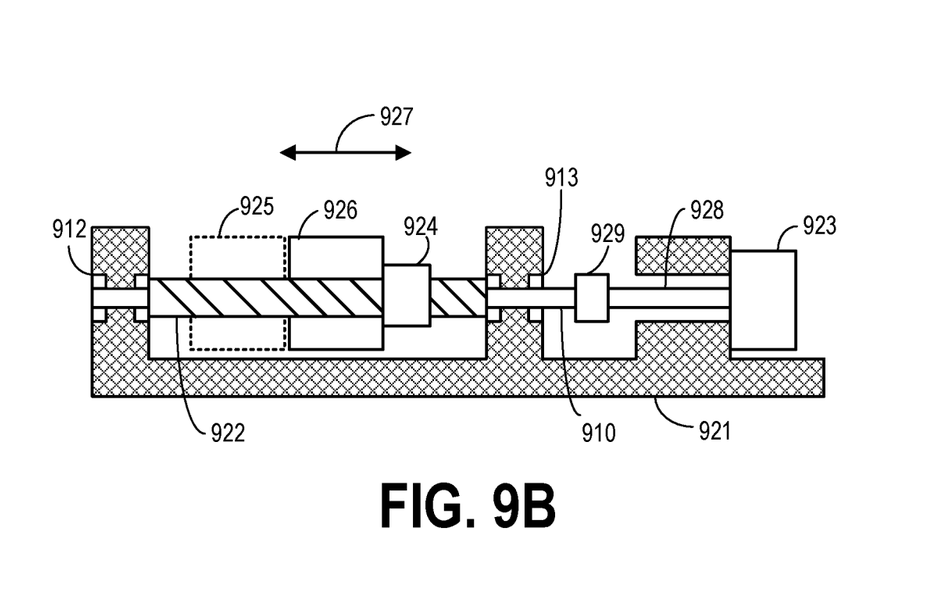
FIG. 9B shows another example configuration of a filter driving system.

FIG. 8C shows a third position of the filter assembly. The x-ray beam transmits though the second filter 806 in the filter housing 810. The filter assembly may transit from the first position or the second position to the third position by actuating the first motor 802 and translating the second filter 806 into the x-ray beam path.

Figure 8D:
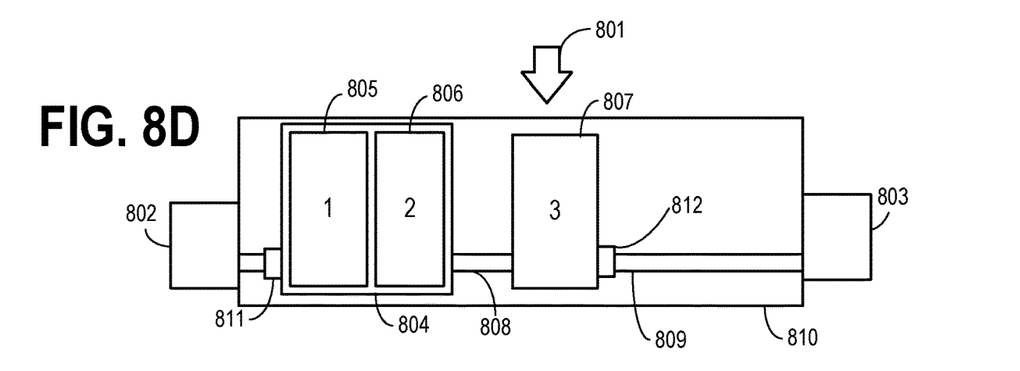
FIG. 8D shows a fourth position of the filter assembly of FIG. 8A.

FIG. 8C shows a fourth position of the filter assembly. The x-ray beam transmits through the third filter 807 in the filter housing 810. The filter assembly may transit from either the second or the third positions to the fourth position by actuating the first motor 802 to translate the housing 804 closer to the first motor 802, and subsequently or simultaneously actuating the second motor 803 to translate the third filter into the x-ray beam path.

Based on the instructions stored in the non-transient memory, the computing device (such as computing device 216 of FIG. 2) may move the filter assembly from any one of the above positions to another position by actuating one or more of the two motors. In one embodiment, two filters are positioned in the filter housing. As one example, the two filters may be coupled to one shaft and driven by one motor. As another example, one of the two filters is coupled to one shaft and driven by one motor, and the other of the two filters is coupled to a second shaft and driven by a second motor. In another embodiment, more than three filters may arranged within the filter housing. For example, the numbers of filters coupled to each shaft are the same, if the total number of filters in the housing is even. The numbers of filters coupled to each shaft is different, if the total number of filters in the housing is odd. As such, duration of filter switching may be reduced due to low average filter distance from the x-ray beam path.

In yet another embodiment, the arrangement of the filters in the filter housing may be based on the type of the filters. Herein, the filter type may be determined by the section of the subject that the filter is designed to image. For example, the first filter used for imaging the first section of the subject and the second filter used or imaging the second section of the subject may be positioned next to each other, if the first section and the second section are connected. The first filter and the second filter may be positioned apart from each other (such as separated by another filter), if the first section and the second section are not connected. As an example, the filter for imaging the abdomen may be positioned next to the filter for imaging the chest, but apart from the filter for imaging the head. In this way, when the chest is imaged after imaging the abdomen, the filters may be quickly switched from one to another. When the head is imaged after imaging the abdomen, the duration for filter switching may be longer, as the imaging subject needs to be physically moved from imaging the abdomen to imaging the head.

FIGS. 9A and 9B show examples of the filter driving system. Each filter assembly (such as filter assembly shown in FIGS. 8A-8D) may have one or more of the filter driving systems.

FIG. 9A shows an example configuration of the filter driving system. Filter 906 is mechanically coupled to a ballscrew nut 904. The ballscrew shaft 902 is mechanically coupled to motor 903 via shaft 908. As motor 903 rotates, the filter 906 may translate in directions indicated by arrow 907 along the ballscrew shaft 902. As such the rotational motion of the shaft is translated to linear motion of the filter along the shaft. The motor is fixed to support 901. A second filter 905 may be coupled to filter 906. The filter 905 and filter 906 are not movable relative to each other. As such, filters 905 and 906 are translated together along the ballscrew shaft 902.

FIG. 9B shows another example configuration of the filter driving system. Filter 926 is mechanically coupled to ballscrew nut 924. The ball screw nut is coupled to motor 923 via shaft 910, flex coupling 929, and shaft 928. The flex coupling is positioned between shaft 910 and shaft 928. Shaft 910 is directly coupled to the ballscrew shaft 922, and shaft 928 is directly coupled to motor 923. The flex coupling may increase the tolerance of misalignment between the motor 923 and the ballscrew shaft 922. The ballscrew shaft 922 is supported by support bearings 912 and 913 at each distal end of the shaft. By rotating the motor 923, the filter 926 may translate in directions as shown by arrow 927. A second filter 925 may be coupled to filter 926. The filter 925 and filter 906 are not movable relative to each other. As such, filters 905 and 906 are translated together along the ballscrew shaft 922.

In other embodiments, the filter may be translated with any one of a rack and pinion, a belt, or a cable-driven system.

The filter driving system in the filter assembly switches one filter to another within two seconds. For example, the filter can be translated 3-5 inches in less than two seconds by the filter driving system.

In this way, mixed-size anatomy may be imaged with high image quality during time-sensitive scans such as contrast enhanced imaging. The technical effect of switching filters after the contrast agent injection is that different anatomies of the subject may be imaged with one contrast agent injection. The technical effect of actuating the motor to switch the filters is that the duration for switching the filters may be reduced. The technical effect of acquiring dataset responsive to contrast enhancement is that the average contrast enhancement in different imaged anatomies may be the same, and the dataset may be displayed with the same dynamic range for diagnostic analysis.

In one embodiment, a method comprises monitoring the contrast enhancement; responsive to a first contrast enhancement being higher than a first threshold, acquiring a first dataset of the imaging subject by transmitting a radiation beam to the imaging subject via a first filter; switching to a different, second filter after acquiring the first dataset; and acquiring a second dataset of the imaging subject by transmitting the radiation beam to the imaging subject via the second filter. In a first example of the method, wherein acquiring the second dataset comprises acquiring the second dataset without additional contrast agent being injected to the imaging subject between the acquisition of the first dataset and the acquisition of the second dataset. A second example of the method optionally includes the first example and further includes wherein both the first filter and the second filter are non-deformable. A third example of the method optionally includes one or more of the first and second examples, and further includes wherein an average contrast enhancement of the injected contrast agent in the imaging subject during the acquisition of the first dataset is substantially the same as an average contrast enhancement of the injected contrast agent in the imaging subject during the acquisition of the second dataset. A fourth example of the method optionally includes one or more of the first through third examples, and further includes, measuring a second contrast enhancement of the injected contrast agent within the imaging subject, and acquiring the second dataset of the imaging subject with the second filter responsive to the second contrast enhancement being less than a second threshold. A fifth example of the method optionally includes one or more of the first through fourth examples, and further includes, wherein both the first threshold and the second threshold are nonzero, and the second threshold is higher than the first threshold. A sixth example of the method optionally includes one or more of the first through fifth examples, and further includes, wherein the first contrast enhancement of the injected contrast agent is a contrast enhancement of the injected contrast agent within a first section of the imaging subject, and the second contrast enhancement of the injected contrast agent is a contrast enhancement of the injected contrast agent within a second section of the imaging subject. A seventh example of the method optionally includes one or more of the first through sixth examples, and further includes, wherein a first section of the imaging subject is imaged while acquiring the first dataset, and a different, second section of the imaging subject is imaged while acquiring the second dataset. An eighth example of the method optionally includes one or more of the first through seventh examples, and further includes, wherein the first section of the imaging subject and the second section of the imaging subject have different anatomies. A ninth example of the method optionally includes one or more of the first through eighth examples, and further includes, wherein switching to the second filter includes operating one or more motors coupled to the first filter and the second filter to translate the first filter out of the radiation beam and translate the second filter into the radiation beam. A tenth example of the method optionally includes one or more of the first through ninth examples, and further includes, displaying the first dataset and the second dataset simultaneously with a same dynamic range.

In a second embodiment, a method comprises measuring a contrast enhancement of an injected contrast agent within an imaging subject; responsive to the contrast enhancement being higher than a first nonzero threshold, acquiring a first number of a first dataset, wherein the first dataset is acquired by transmitting a radiation beam to the first section of the imaging subject via a first filter; switching to a different, second filter after acquiring the first number of the first datasets; acquiring second number of a second dataset by transmitting the radiation beam to a different, second section of the imaging subject via the second filter, wherein the contrast enhancement of the injected contrast agent with in the imaging subject is higher than the first threshold while acquiring the second number of the second datasets. In a first example of the method, the first number is the same as the second number. A second example of the method optionally includes the first example and further includes determining a time point to start acquiring each of the first and second datasets based on the contrast enhancement of the injected contrast agent within the imaging subject. A third example of the method optionally includes one or more of the first and second examples, and further includes wherein the first filter and the second filter are bowtie filters.

In a third embodiment, an imaging system comprises a gantry for receiving an imaging subject; a radiation source positioned in the gantry for emitting radiation exposure; a detector positioned on the opposite of the gantry relative to the radiation source; a filter housing mounted to the gantry; a first filter and a second filter positioned in the filter housing; a filter driving system for switching filters by moving filters into or out of the radiation exposure; a motorized table for moving an imaging subject; and a computation device with instructions stored in a non-transient memory, the computation device may execute the instructions to: emit radiation exposure via the radiation source; move the imaging subject via the motorized table at a nonzero speed; while moving the imaging subject, acquire a dataset of the imaging subject by detecting the emitted radiation exposure transmitted through the imaging subject via the detector, wherein a first filter is positioned within the emitted radiation exposure, between the radiation source and the imaging subject; and while acquiring the dataset, estimate the anatomy of the imaging subject, responsive to a change in the anatomy, operate the filter driving system to switch the first filter with the second filter, wherein during filter switching, the radiation source does not emit radiation exposure. In a first example of the imaging system, the computation device may execute the instructions to further monitor a contrast enhancement of an injected contrast agent, and start acquiring the dataset responsive to the contrast enhancement higher than a nonzero threshold. A second example of the imaging system optionally includes the first example and further includes, wherein the filter driving system includes a motor coupled to the first filter and the second filter via a shaft, and switching the first filter with the second filter includes actuating the motor to translate the first filter out of the radiation beam, and translate the second filter into the radiation beam. A third example of the imaging system optionally includes one or more of the first and second examples, and further includes, wherein the first filter is different from the second filter, and the acquired dataset are from a plurality of different anatomies of the imaging subject. A fourth example of the imaging system optionally includes one or more of the first and third examples, and further includes wherein a duration for switching the first filter to the second filter is less than two seconds.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein". Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    acquiring a first dataset of a first region of interest of an imaging subject in a first scan by transmitting a radiation beam to the imaging subject via a first filter, wherein the first filter is determined based on an anatomy of the first region of interest;
    switching to a second filter after acquiring the first dataset, wherein the first filter and the second filter are different filters; and
    acquiring a second dataset of a different, second region of interest of the imaging subject in a second scan by transmitting the radiation beam to the imaging subject via the second filter;
    wherein the second filter is determined based on anatomy of the second region of interest;
    wherein switching from the first filter of the first scan to the second filter of the second scan is time sensitive; and
    wherein switching from the first filter to the second filter takes less than two seconds.

2. The method of claim 1, wherein both the first filter and the second filter are non-deformable.

3. The method of claim 1, wherein the first filter and the second filter are bowtie filters.

4. The method of claim 1, wherein the first region of interest of the imaging subject and the second region of interest of the imaging subject are of different anatomies.

5. The method of claim 1, wherein switching to the second filter includes operating one or more motors coupled to the first filter and the second filter to translate the first filter out of the radiation beam and translate the second filter into the radiation beam.

6. A method, comprising:
    responsive to a contrast enhancement of an injected contrast agent within an imaging subject, acquiring a first dataset of a first region of interest of the imaging subject in a first scan, wherein the first dataset is acquired by transmitting an X-ray beam to the first region of interest of the imaging subject via a first filter wherein the first filter is determined based on an anatomy of the first region of interest;
    switching to a second filter after acquiring the first dataset; and
    acquiring a second dataset of a different, second region of interest of the imaging subject in a second scan by transmitting the X-ray beam to the second region of interest of the imaging subject via the second filter;
    wherein the first filter and the second filter are different filters;
    wherein the second filter is determined based on the second region of interest;
    wherein switching from the first filter of the first scan to the second filter of the second scan is time sensitive; and
    wherein switching from the first filter to the second filter takes less than two seconds.

7. The method of claim 6, further comprising determining a time point to start acquiring each of the first and the second datasets based on the contrast enhancement of the injected contrast agent within the imaging subject.

8. The method of claim 6, wherein the first filter and the second filter are bowtie filters.

* * * * *